US009750470B2

(12) United States Patent
Jun et al.

(10) Patent No.: US 9,750,470 B2
(45) Date of Patent: Sep. 5, 2017

(54) ALIGNING BITE OF X-RAY DEVICE AND X-RAY DEVICE HAVING THE SAME

(71) Applicant: Genoray Co., LTD., Seongnam-si, Gyeonggi-do (KR)

(72) Inventors: Jin-Hwan Jun, Anyang-si (KR); Kyung Hoon Kim, Seoul (KR)

(73) Assignee: GENORAY CO., LTD., Seongnam-si, Gyeonggi-Do (KR)

( * ) Notice: Subject to any disclaimer, the term of this patent is extended or adjusted under 35 U.S.C. 154(b) by 388 days.

(21) Appl. No.: 14/641,451

(22) Filed: Mar. 9, 2015

(65) Prior Publication Data
US 2015/0335300 A1    Nov. 26, 2015

(30) Foreign Application Priority Data

May 23, 2014  (KR) ........................ 10-2014-0062221

(51) Int. Cl.
| | | |
|---|---|---|
| *H05G 1/00* | (2006.01) | |
| *A61B 6/04* | (2006.01) | |
| *A61B 6/14* | (2006.01) | |
| *A61B 6/03* | (2006.01) | |
| *A61B 6/00* | (2006.01) | |

(52) U.S. Cl.
CPC .............. *A61B 6/145* (2013.01); *A61B 6/00* (2013.01); *A61B 6/03* (2013.01); *A61B 6/035* (2013.01); *A61B 6/04* (2013.01); *A61B 6/14* (2013.01); *A61B 6/505* (2013.01); *A61B 6/4085* (2013.01)

(58) Field of Classification Search
CPC .......... A61B 90/16; A61B 6/14; A61B 6/145; A61B 6/4233; A61B 6/501; A61B 6/4435; G03B 42/042
USPC .............. 378/38, 70, 168, 205, 208; 433/29
See application file for complete search history.

(56) References Cited

U.S. PATENT DOCUMENTS

| | | | |
|---|---|---|---|
| 4,530,367 A | | 7/1985 | Desjardins et al. |
| 8,876,375 B2 * | | 11/2014 | Laude ................ A61B 6/4283 378/170 |
| 9,456,792 B2 * | | 10/2016 | Grant ...................... A61B 6/04 |
| 2010/0150316 A1 | | 6/2010 | Thoms |
| 2010/0204578 A1 | | 8/2010 | Schmidt et al. |
| 2011/0036356 A1 | | 2/2011 | Arn et al. |

FOREIGN PATENT DOCUMENTS

| | | |
|---|---|---|
| JP | 10-314165 A | 12/1998 |
| JP | 2010-524603 A | 7/2010 |
| JP | 2010-214023 A | 9/2010 |

(Continued)

*Primary Examiner* — Don Wong
(74) *Attorney, Agent, or Firm* — Revolution IP, PLLC

(57) ABSTRACT

An aligning bite of an X-ray device for aligning a subject to an X-ray imaging point and an X-ray device having the same are disclosed. The aligning bite of an X-ray may include a support unit being rotatably connected to a bite stand supporting the aligning bite, and a bite unit being rotatably connected to the support unit, wherein the support unit may include a link frame supporting the bite unit by connecting the bite unit to the bite stand, a first joint rotatably connecting one side of the link frame to the bite stand, a second joint rotatably connecting the bite unit to another side of the link frame, and a third joint being provided between the first joint and the second joint so as to allow the link frame to be folded.

13 Claims, 9 Drawing Sheets

(56) References Cited

FOREIGN PATENT DOCUMENTS

| KR | 10-2005-0000934 A | 1/2005 |
| KR | 10-2008-0014769 A | 2/2008 |
| KR | 10-2012-0140102 A | 12/2012 |

* cited by examiner (a)

(b)

ALIGNING BITE OF X-RAY DEVICE AND X-RAY DEVICE HAVING THE SAME

This application claims the benefit of the Korean Patent Application No. 10-2014-0062221, filed on May 23, 2014, which is hereby incorporated by reference as if fully set forth herein.

BACKGROUND OF THE INVENTION

Field of the Invention

The present invention relates to an aligning bite of an X-ray device and an X-ray device having the same, wherein the aligning bite, which is included in an X-ray device acquiring images of subjects by using X-rays, aligns a subject to an imaging point and, more particularly, to an aligning bite of an X-ray device and an X-ray device having the same, wherein the aligning bite is capable of accurately positioning an area of interest that requires image information in an imaging focus area (or focus point).

Discussion of the Related Art

Generally, an X-ray imaging device (hereinafter referred to as "X-ray device") refers to a device configured to acquire projection data respective to an imaging subject (hereinafter referred to as "subject"), by using the characteristic of X-ray intensity being attenuated in accordance with the physical nature of the subject and a distance between the subject and the device, when X-rays pass through the subject, and to convert the acquired data to image (i.e., to perform imaging on the acquired data). For example, when radiating X-rays to a human being, a projection image showing the inside of the human body by using a variation of attenuation coefficients in accordance with different types and characteristics of biological tissue.

Additionally, the X-ray device is configured to include an X-ray generator radiating (or emitting) X-rays to a subject so that the X-rays can pass through the subject, and a detector detecting the X-rays that have passed through the subject. The X-ray generator and the detector are generally equipped to a supporting apparatus, such as an arm, which is configured to support the X-ray generator and the detector. And, the X-ray generator and the detector are configured to face into one another, thereby being capable of acquiring image information of the subject while rotating around the subject. An X-ray Computed Tomography (CT) Imaging Device may be given as an example of the above-described X-ray device, and, herein, the X-ray CT imaging device generates a sectional image of the subject by performing an image reconfiguration process, wherein the device acquires projection data by radiating X-rays on the subject at different angles and reconfigures a sectional image from the acquired projection data.

3-dimensional (3D) Cone Beam Computed Tomography (CBCT) technology has already been introduced to fields of dental imaging and Mammography, and a panoramic imaging device, which corresponds to another example of the X-ray device, is being used for acquiring images of teeth and tissue surrounding the teeth. In the panoramic imaging device, the X-ray generator and the detector are equipped to an arm so as to face into one another. The arm performs linear movements and rotational movements (or rotating movements) in accordance with operations of a driving unit, and, accordingly, as the X-ray generator and the detector moves around the subject along a predetermined trajectory, the panoramic imaging device performs imaging.

Referring to FIG. 1, the related art panoramic imaging device includes an X-ray generator 10 and a detector 20, which are spaced apart from one another and positioned to face into one another. And, the X-ray generator 10 and the detector 20 collectively acquire the projection data respective to a subject 1 by rotating around the subject 1.

The X-ray generator 10 and the detector 20 are equipped to an arm 30, and the arm 30 is rotatably fixed to a driving unit 40 of a device body 50, thereby being capable of performing linear movements and rotational movements. The device body 50 is configured to include a post frame 51 supporting the driving unit 40, and a support 52 being provided to prevent the post frame 51 from falling or being tipped over. And, the device body 50, and, most particularly, the post frame 51 is provided with an aligning bite 61, which is configured to appropriately position the subject to an X-ray imaging point.

More specifically, the aligning bite 61 is equipped to a bite stand 53, which is provided on the post frame 51, and the bite stand 53 is provided with the aligning bite 61 and a chin rest 62. Accordingly, in order to perform panoramic imaging, when a subject of examination (i.e., examinee) places his (or her) chin on the chin rest 62 and bites on the aligning bite 61 with his (or her) teeth, thereby assuming a stably fixed position, the X-ray generator 10 and the detector 20, which are equipped to the arm 30, move and acquire the respective projection data.

Meanwhile, in order to acquire information on hard tissue (alveolar bone) of a particular topical area (or area of interest), e.g., sectional information, such as height, thickness, and so on, of the alveolar bone located at an anterior teeth area or molar areas, the panoramic imaging device acquires image information of the area of interest, e.g., a sectional image, such as a cross-sectional slice of the area of interest, by performing a process of acquiring projection data respective to the area of interest from multiple angles and reconfiguring the acquired projection data, and such information is used as information for performing dental surgery, e.g., implant surgery and diagnosis.

In the above-described related art X-ray device, the aligning bite 61 is configured to be fixed in its place or to rotate in its place based upon an axis, which passes through the bite support 53. And, accordingly, as shown in FIG. 2, projection data respective to such areas of interest $I_1$, $I_2$, and $I_3$ from diverse locations (or location points) may be acquired.

However, according to the related art aligning bite, as shown in FIG. 3, positions of the X-ray generator 10 and the detector 20 are required to be changed noticeably in an imaging mode that can image the anterior teeth area $I_1$ ((a) of FIG. 3) and in an imaging mode that can image the molar areas $I_2$ and $I_3$, e.g., left and right molar areas $I_2$ ((b) of FIG. 3). And, since the X-ray generator 10 and the detector 20 are required to be excessively moved (or repositioned) in order to perform imaging of the molar areas after performing imaging of the anterior teeth area, numerous problems may occur in that a broader operating range of the arm 30 is required, that a driving mechanism of the arm 30 becomes complicated, and that a long period of time is consumed for imaging the area of interest, not to mention that, since it is impossible to perform imaging on an area exceeding the predetermined operating range of the arm 30, the imaging range becomes limited.

RELATED ART DOCUMENTS

Patent Documents (Patent Document 1) Published Korean Patent Application No. 10-2012-0140102, published on Dec. 28, 2012)

(Patent Document 2) Published Korean Patent Application No. 10-2008-0014769, published on Feb. 14, 2008)

(Patent Document 3) Published Korean Patent Application No. 10-2005-0000934, published on Jan. 6, 2005)

SUMMARY OF THE INVENTION

Accordingly, the present invention is directed to an aligning bite of an X-ray device and an X-ray device having the same that substantially obviate one or more problems due to limitations and disadvantages of the related art.

An object of the present invention is to provide an aligning bite of an X-ray device and an X-ray device having the same that can accurately align an area of interest to an imaging focus point in order to allow accurate image information to be acquired with respect to multiple areas of interest each corresponding to a different location point (or position).

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve these objects and other advantages and in accordance with the purpose of the invention, as embodied and broadly described herein, the present invention provides an aligning bite of an X-ray device for aligning a subject to an X-ray imaging point and an X-ray device having the same. According to an exemplary embodiment of the present invention, the aligning bite of the X-ray device may be configured to include a support unit being rotatably connected to a bite stand supporting the aligning bite, and a bite unit being rotatably connected to the support unit. Additionally, the support unit may be configured to include a link frame supporting the bite unit by connecting the bite unit to the bite stand, a first joint rotatably connecting one side of the link frame to the bite stand, a second joint rotatably connecting the bite unit to another side of the link frame, and a third joint being provided between the first joint and the second joint so as to allow the link frame to be folded.

The link frame may be configured to include a first link member being connected to the bite stand by the first joint, and a second link member being connected to the first link member by the third joint. And, according to the exemplary embodiment of the present invention, the second link member may be connected to the bite unit by the second joint.

The bite unit may be configured to include a bite support stand being rotatably connected to the link frame by the second joint, and a bite piece being mounted to the bite support stand so as to be bitten between upper teeth and lower teeth of an examinee (or subject of examination).

The bite piece may have an arched shape respective to a dental arch form, and the bite piece may be mounted to the bite support stand so as to allow a height of the bite piece to be adjusted. Additionally, the bite support stand may be configured of a first bite mounting part and a second bite mounting part each supporting the bite piece at different heights. And, a plurality of pass-through holes may be formed on the bite piece.

Additionally, a fastening holder may be equipped to the support unit so as to simultaneously lock the first joint, the second joint, and the third joint. And, more specifically, the fastening holder may maintain a position of the aligning bite by simultaneously locking movements of the link frame and the bite unit.

According to another exemplary embodiment of the present invention, an X-ray device may be configured to include an aligning bite of the X-ray device aligning a subject to an X-ray imaging point, an X-ray generator emitting X-ray beams toward the subject, and a detector moving while being in a state of facing into the X-ray generator. And, herein, the aligning bite may be configured to include a support unit being rotatably connected to a bite stand supporting the aligning bite, and a bite unit being rotatably connected to the support unit. And, herein, the support unit may be configured to include a link frame supporting the bite unit by connecting the bite unit to the bite stand, a first joint rotatably connecting one side of the link frame to the bite stand, a second joint rotatably connecting the bite unit to another side of the link frame, and a third joint being provided between the first joint and the second joint so as to allow the link frame to be folded.

It is to be understood that both the foregoing general description and the following detailed description of the present invention are exemplary and explanatory and are intended to provide further explanation of the invention as claimed.

BRIEF DESCRIPTION OF THE DRAWINGS

The characteristics and advantages of the present invention may be understood more easily with the detailed description of the exemplary embodiments of the present invention, which will hereinafter be provided, along with the accompanying drawings, which will be briefly described as follows. In the drawings.

DETAILED DESCRIPTION OF THE INVENTION

Figure 1:
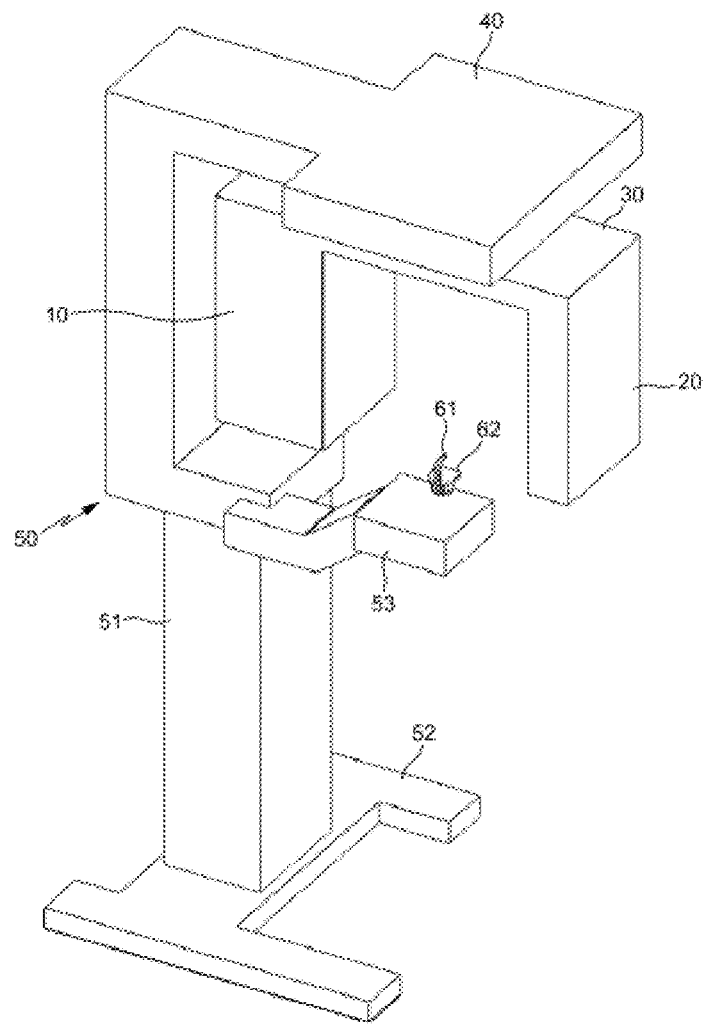
FIG. 1 illustrates a perspective view showing an example of a general X-ray device having an aligning bite.
Figure 2:
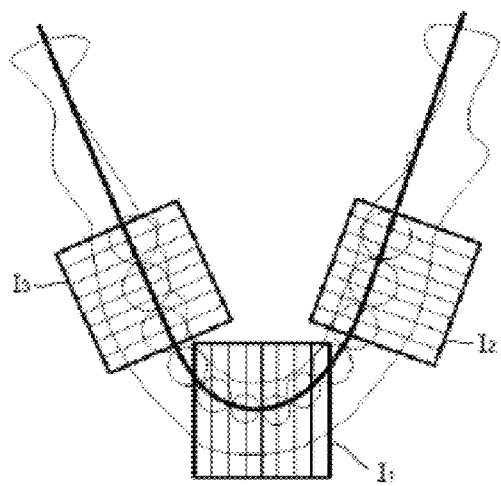
FIG. 2 illustrates an exemplary area of interest of a jaw bone being a subject of imaging.
Figure 3:
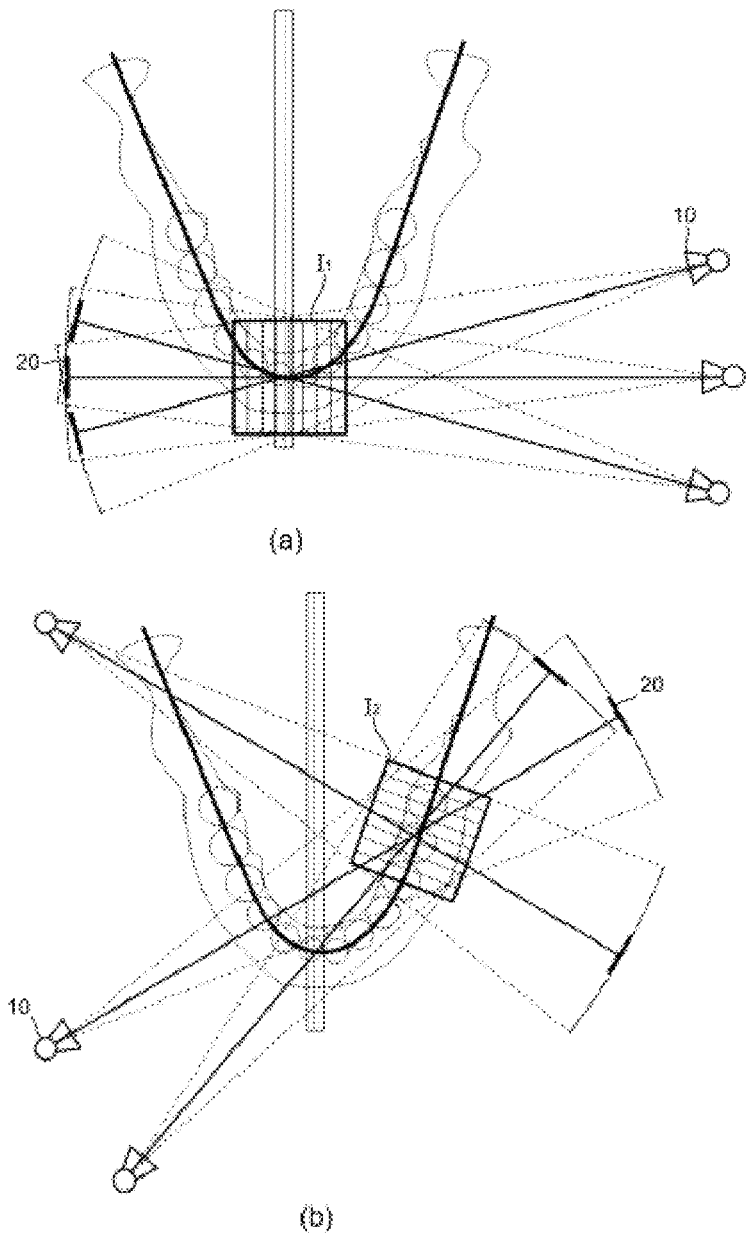
FIG. 3 illustrates an exemplary method of acquiring projection data respective to an anterior teeth area and a (left) molar area by using the related art aligning bite.

Hereinafter, preferred embodiments of the present invention, through which objects of the present invention can be realized in detail, will be described in more detail with reference to the accompanying drawings. In describing the exemplary embodiment of the present invention, identical reference numerals will be used for identical components shown in the drawings, and repeated description of identical components will be omitted for simplicity.

First of all, an exemplary embodiment of an X-ray device that can realize an imaging method of the X-ray device according to the present invention will be described in detail with reference to FIG. 4 to FIG. 6. Herein, FIG. 4 illustrates a perspective view showing an example of an X-ray device having an aligning bite according to an exemplary embodiment of the present invention, FIG. 5 illustrates a perspective view showing an aligning bite according to an exemplary embodiment of the present invention, and FIG. 6 illustrates a perspective view of an exemplary folded structure of the aligning bite shown in FIG. 5.

Figure 4:
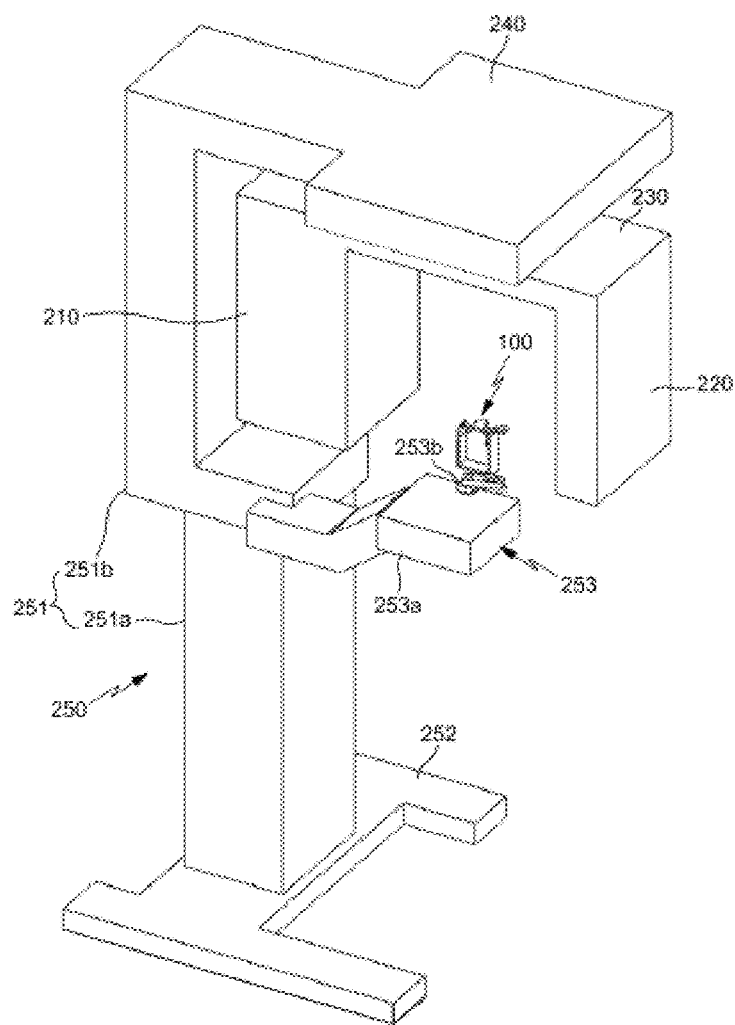
FIG. 4 illustrates a perspective view showing an example of an X-ray device having an aligning bite according to an exemplary embodiment of the present invention.
Figure 5:
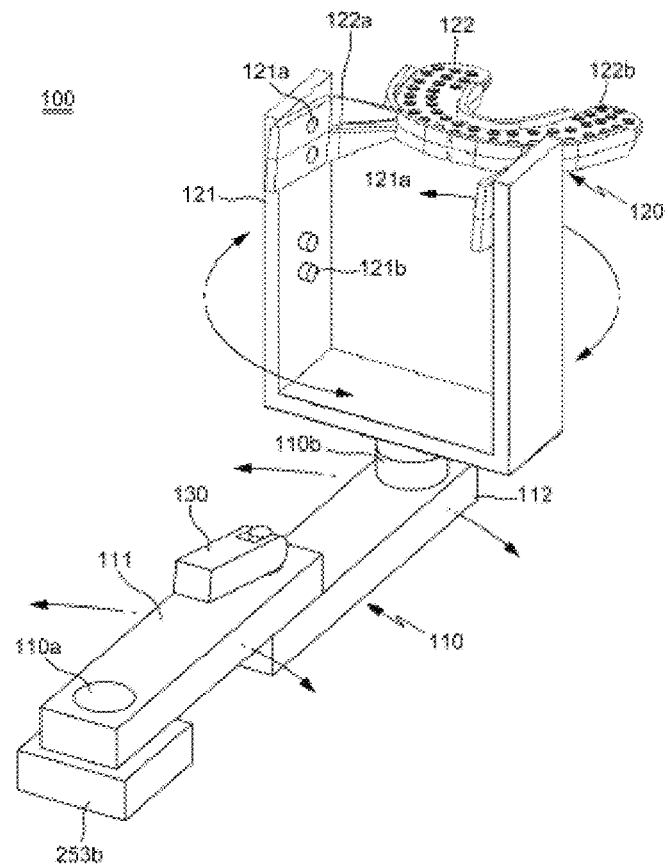
FIG. 5 illustrates a perspective view showing an aligning bite according to an exemplary embodiment of the present invention.
Figure 6:
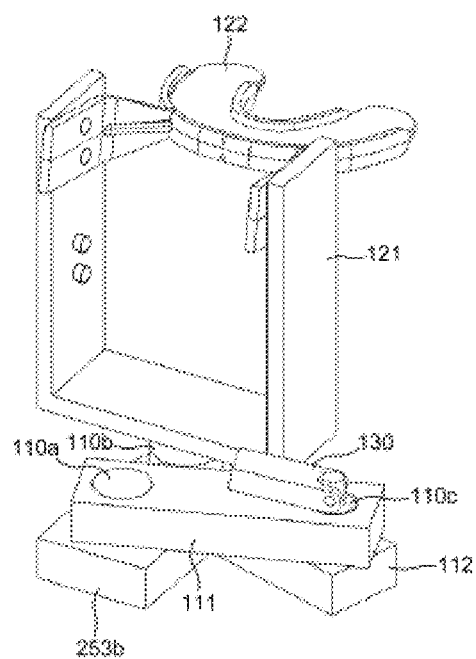
FIG. 6 illustrates a perspective view of an exemplary folded structure of the aligning bite shown in FIG. 5.

Referring to FIG. 4 to FIG. 6, the present invention provides an aligning bite of an X-ray device that can align a subject of image to an X-ray imaging point and an X-ray device having the same.

The X-ray device according to the exemplary embodiment of the present invention is configured to include the aligning bite 100, an X-ray generator 210 emitting X-ray and, more particularly, an X-ray beam toward a subject, and a detector 220 being installed to face into the X-ray generator 210 and detecting the X-ray.

More specifically, according to the exemplary embodiment of the present invention, the X-ray generator 210 and the detector 220 are equipped to an arm 230, i.e., a suspension arm, and the arm 230 rotatably supported to a driving unit 240 of a device body, thereby being capable of performing linear movements and rotational movements.

In this exemplary embodiment, the device body 250 is configured as a stand further including a post frame 251 supporting the driving unit 240, and a support 252 preventing the post frame 251 from falling or being tipped over. And, herein, the X-ray device being disclosed in this exemplary embodiment corresponds to an example of a panoramic imaging device.

The post frame 251 is configured to include a lower frame 251a being installed on the support 252, and an upper frame 251b being installed on an upper portion of the lower frame 251a so as to support the driving unit 240.

The driving unit 240 may be directly installed on the upper frame 251b or may be indirectly installed on the upper frame 251b by being installed on a connection block, which functions as its connection medium, and the inside of the driving unit 240 is equipped with a device, such as a gear allowing the arm 230 to perform movements, e.g., linear movements and rotational movements. Since a technology that has already been disclosed in this technical field may be applied to the structures, such as the driving unit 240, the arm 230, the post frame 251, and so on, and to the operating principle and image acquiring principle of the X-ray generator 210 and the detector 220, additional description will be omitted for simplicity.

Additionally, the aligning bite 100 is mounted to a bite stand 253 so as to be supported by the bite stand 253. In this exemplary embodiment, although the bite stand 253 is equipped to the post frame 251 in order to support the aligning bite 100, the present invention will not be limited only to this.

In this exemplary embodiment, the bite stand 253 is configured to include a fixed base 253a being fixed to the post frame 251, and a bite connector 253b being equipped to the fixed base 253a and rotatably supporting the aligning bite 100. Alternatively, however, the aligning bite 100 may also be directly and rotatably connected to the fixed base 253a.

Referring to FIG. 5 and FIG. 6, the aligning bite 100 according to the exemplary embodiment of the present invention is configured to include a support unit 110 being rotatably connected to the bite stand, and a bite unit 120 being rotatably connected to the support unit 110, and, in this structure, at least 3 joints have been applied. Accordingly, 3 joints or a larger number of joints may be applied to the present invention.

Additionally, the support unit 110 is configured to include a link frame 111 and 112 connecting the bit stand 253 to the bite unit 120, a first joint 110a rotatably connecting one side of the link frame 111 and 112 to the bite stand 253, a second joint 110b rotatably connecting the bite unit 120 to another side of the link frame 111 and 112, and a third joint 110c being equipped between the first joint 110a and the second joint 110b so as to allow the link frame 111 and 112 to be folded.

The link frame 111 and 112 is rotatably connected to the bite stand 253 through the first joint 110a as its connection medium, thereby being capable of supporting the bite unit 120.

More specifically, the link frame 111 and 112 is configured to include a first link member 111 being connected to the bite stand 253 through the first joint 110a, and a second link member 112 being connected to the first link member 111 through the third joint 110c.

In this exemplary embodiment, the second link member 112 is connected to the bite unit 120 through the second joint 110b, and the first link member 111 is connected to the bite connector 253b through the first joint 110a. Accordingly, the aligning bite 100 according to the exemplary embodiment of the present invention may be configured of a 3-joint structure or, as described above, the aligning bite 100 may be configured of a multiple joint structure being configured of three or more joints.

Additionally, each of the first link member 111 and the second link member 112 is configured in the form (or shape) of a bar, and the first link member 111 is connected to an upper portion of the bite connector 253b, and the second link member 112 is connected to a lower portion of the first link member 111. However, the shape or structure of the link frame 111 and 112 will not be limited only to the example described above, and, in this exemplary embodiment, the first joint 110a, the second joint 110b, and the third joint 110c collectively correspond to a pivot structure configuring a straight rotation axis.

Subsequently, the bite unit 120 is configured to include a bite support stand 121 being rotatably connected to the link frame 111 and 112 and, most particularly, to the second link member 112 through the second joint 110b, and a bite piece 122 being equipped to the bite support stand 121 so that an examinee can bite on the bite piece 122 with his (or her) upper teeth and lower teeth.

The bite piece 122 may have an arch shape (or form) in accordance with the shape of a dental arch of a human being. And, it is preferable that the bite piece 122 can have its height adjusted, and, in order to do so, the bite piece 122 may be equipped to the bit support stand 121 so that its height can be adjusted.

In this exemplary embodiment, the bite piece 122 is detachably fixed to the bite support stand 121. More specifically, the bite support stand 121 is provided with a bite mounting unit 121a and 121b, which is configured to mount the bite piece 122 to the bite support stand 121. And, herein, the bite mounting unit 121a and 121b may be configured to include a first bite mounting part 121a and a second bite mounting part 121b each supporting the bite piece 122 at different heights. Accordingly, the height of the bite piece 122 may be adjusted in accordance with a jaw structure of the examinee.

The bite mounting unit 121a and 121b is configured to have the shape of a protrusion protruding from a surface of the bite support stand 121, and the bite piece 122 may be provided with an assembly hole, to which the bite mounting unit 121a and 121b can be fit. However, the mounting structure of the bite piece 122 will not be limited only to the above-described structure.

In this exemplary embodiment, the bite piece 122 includes a piece connector 122a, which is configured to connect a bite piece body, i.e., a portion of the bite piece 122 being bitten between the upper teeth and the lower teeth of the examinee (the arch-shaped portion) to the bite support stand 121. And, herein, the bite piece 122 and, most particularly, the piece body may be provided with a plurality of pass-through holes 122b.

Since the bite piece 122 may also be configured to perform up-and-down movements (or vertical movements) along a rail of the bite support stand 121, the height adjustment structure of the bite piece 122 will not be limited only to the exemplary structure, which is described above.

Additionally, the aligning bite 100 may be provided with a fastening holder 130, which can maintain a position of the link frame 111 and 112 by locking the link frame 111 and 112. And, although the fastening holder 130 can be configured to be capable of simultaneously locking multiple joints, it will be evident that the present invention will not be limited to such structure.

By simultaneously locking the first joint 110a to the third joint 110c, the fastening holder 130 prevents the aligning bite 100 from moving. More specifically, the fastening holder 130 maintains the position of the aligning bite 100 by simultaneously locking the movements of the support frame 110 and the bite unit 120, and, accordingly, all of the joints provided in the aligning bite may be simultaneously locked by the fastening holder 130.

Figure 7A:
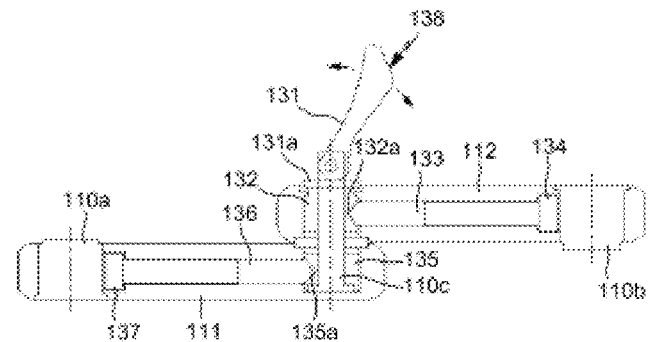
FIG. 7a and FIG. 7b illustrate an internal structure of the aligning bite shown in FIG. 5.
Figure 7B:
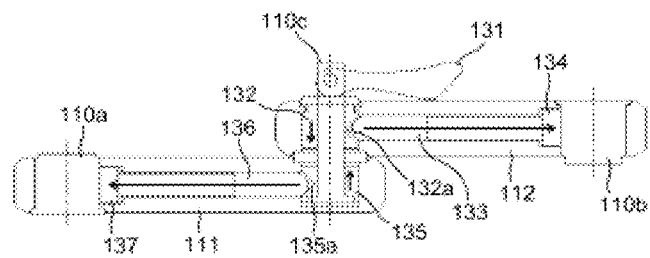

Referring to FIG. 7a and FIG. 7b, the fastening holder 130 according to the exemplary embodiment of the present invention is configured to include a holder switch 131, a first push 132, a first brake 133 and 134, a second push 135, and a second brake 136 and 137.

The holder switch 131 is rotatably connected to the third joint 110c, thereby being capable of moving the first push 132 and the second push 135. Herein, the first push 132 applies pressure on the second joint 110b by pushing the first brake 133 and 134, and the second push 132 applies pressure on the first joint 110a by pushing the second brake 136 and 137.

More specifically, the third joint 110c is installed by passing through the first push 132 and the second push 135. And, when the holder switch 131 is pressed (or pushed), a pressure plate 131a provided between the holder switch 131 and the first push 132 is pressed by the holder switch 131, thereby causing the third joint 110c to be pulled due to its reaction force.

Accordingly, the first push 132 and the second push 135 moves along an axial direction of the third joint 110c, and, due to the first push 132 and the second push 135, each of the first brake 133 and 134 and the second brake 136 and 137 is pushed so as to come in contact with the second joint 110b and the first joint 110a, respectively.

For example, as shown in FIG. 7b, the first push 132 descends (or moves downward) by being pressed by the pressure plate 131a, and the second push 135 elevates (or moves upward) by receiving pressure from the pressure plate 131a, and, during this process, the first brake 133 and 134 and the second brake 136 and 137 are respectively pushed toward the second joint 110b and the first joint 110a, thereby locking the first joint 110a to the third joint 110c at the same time.

An inclined groove 132a having one end of the first brake 133 and 134 inserted therein is formed in the first push 132, and an inclined groove 135a having one end of the second brake 136 and 137 inserted therein is formed in the second push 135. And, when the first push 132 and the second push 135 move along the axial direction of the third joint 110c due to a change in the position of the holder switch 131, the end of the first brake 133 and 134 and the end of the second brake 136 and 137 are pushed outside of the third joint 110c from the inclined groove 132a of the first push 132 and the inclined groove 135a of the second push 135 by making sliding movements. In this exemplary embodiment, although the shapes of the inclined groove 132a of the first push and the inclined surface 135a of the second push correspond to triangular grooves, the shapes of the inclined grooves will not be limited only to this, and, therefore, as long as the inclined grooves perform the same functions, the inclined grooves may be formed to have diverse shapes.

In this exemplary embodiment, each of the first brake 133 and 134 and the second brake 136 and 137 is configured to include a brake bar 133 and 136, each being movably installed respectively inside the second link member 112 and the first link member 111 along a length direction, and a pressure applying pad 134 and 137, each selectively coming into contact with the second joint 110b and the first joint 110a, respectively, thereby respectively applying pressure on the second joint 110b and the first joint 110a.

According to the aligning bite 100 disclosed in the exemplary embodiment, areas being positioned at an X-ray imaging focus point ('+' areas in FIG. 8 to FIG. 10) may be diversely changed/adjusted by the joint structure, and the X-ray imaging focus point may be formed by an aiming light source (not shown) being equipped to the device body 250 so as to create crossover light.

Figure 8:
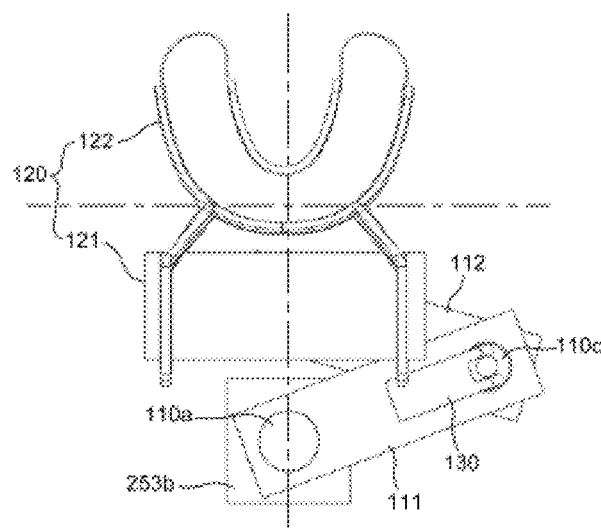
FIG. 8 to FIG. 10 respectively illustrate plane views of the aligning bite shown in FIG. 5 being adjusted in order to be place areas of interest respective to different locations within an imaging focus area.
Figure 9:
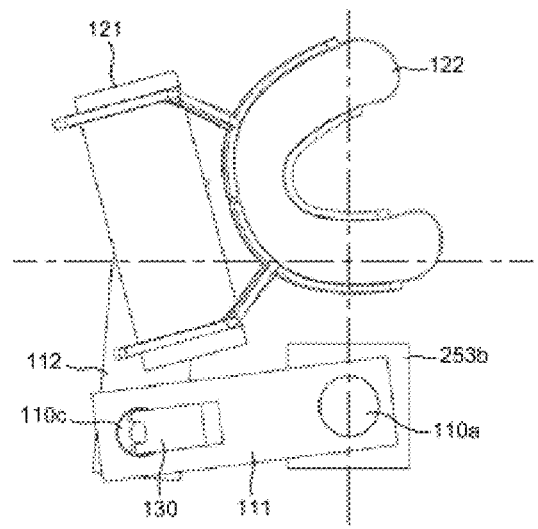
Figure 10:
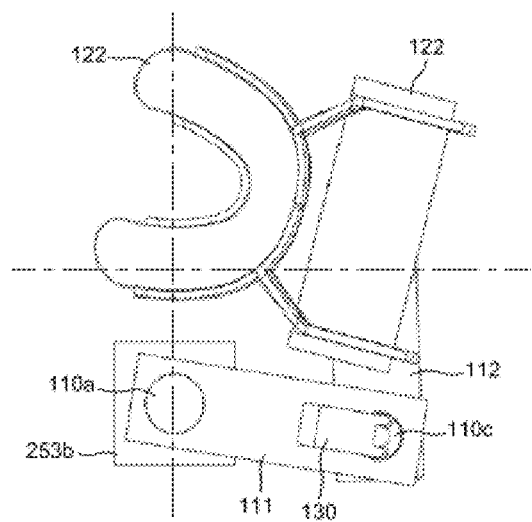

FIG. 8 illustrates a state when the aligning bite 100 is adjusted to allow the anterior teeth area of the examinee to be aligned to the imaging focus point, FIG. 9 illustrates a state when the aligning bite 100 is adjusted to allow the left molar area of the examinee to be aligned to the imaging focus point, and FIG. 10 illustrates a state when the aligning bite 100 is adjusted to allow the right molar area of the examinee to be aligned to the imaging focus point. And, herein, according to the exemplary embodiment of the present invention, since the portion on which imaging is intended to be performed, i.e., the area of interest may be accurately aligned to the imaging point, i.e., imaging focus point, the operating ranges of the X-ray generator and the generator may be reduced, and highly accurate images may be acquired within a short period of time.

In order to perform imaging of the area of interest, a dental impression material is deposited on the bite piece 122 in order to acquire a molding of the examinee's dental structure. Thereafter, the bite piece 122 having the dental impression material deposited thereon is mounted to the bite support stand 121. Subsequently, X-ray imaging is performed after aligning the area of interest to the imaging focus point by rotating the link frame 111 and 112.

Figure 11:
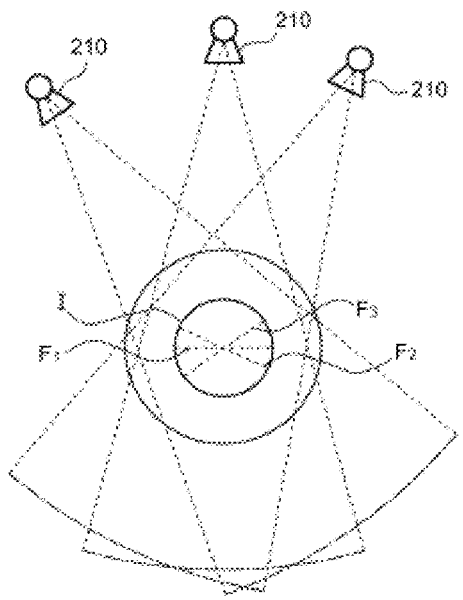
FIG. 11 illustrates an example of acquiring projection data of an area of interest from multiple directions by using the X-ray device according to an exemplary embodiment of the present invention.
Figure 12:
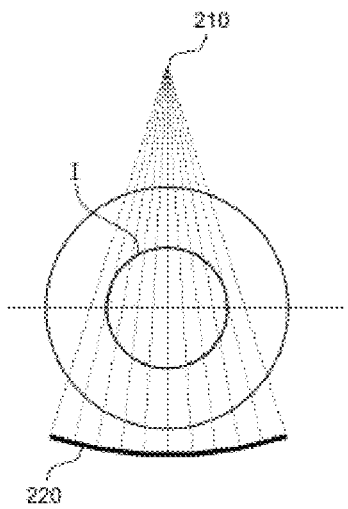
FIG. 12 illustrates an example of acquiring projection data respective to an entire area of interest from a single direction by using a detector having a small (or narrow) width.
Figure 13:
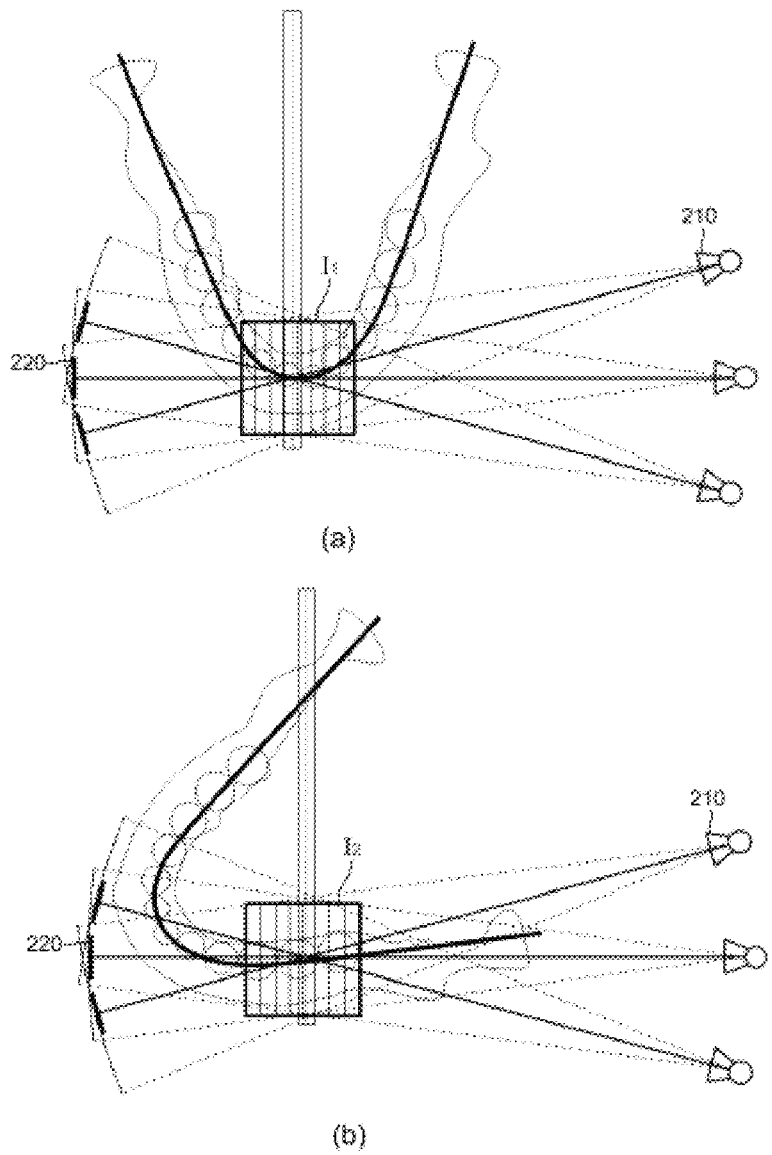
FIG. 13 illustrates an exemplary method of acquiring projection data respective to an anterior teeth area and a (left) molar area by using an aligning bite according to an exemplary embodiment of the present invention.

Referring to FIG. 11 to FIG. 13, in order to acquire image information, e.g., a sectional image or three-dimensional (3D) image of the area of interest I, which is positioned on the imaging focus point, when imaging is performed at different direction on the entire area of interest I, and when projection data respective to the entire area of interest I is acquired from each direction, image information, e.g., a cross-sectional slide image of the area of interest is created by using an image reconfiguration method. In FIG. 11, $F_1$, $F_2$, and $F_3$ respectively represent focal planes corresponding to each imaging direction.

In the above-described X-ray imaging process, the projection data respective to the area of interest from any one direction may be acquired by a detector having a surface area that can cover the entire area of interest I, and, alternatively, the projection data may also be acquired by being divided into sub-projection data of small areas and acquired by a detector having a narrow surface area that can cover only a portion of the area of interest I, as shown in FIG. 12.

Referring to FIG. 13, areas of interest corresponding to different positions may be aligned to the same imaging focus point by using the aligning bite 100 according to the exemplary embodiment of the present invention, and, accordingly, the operating ranges of the X-ray device 210 and the detector 220 may be minimized, and, when imaging is performed on areas of interest corresponding to different location points (or positions), the driving mechanism of the X-ray device and the detector and, most particularly, the driving mechanism of the arm 230 may be identically configured.

Figure 14:
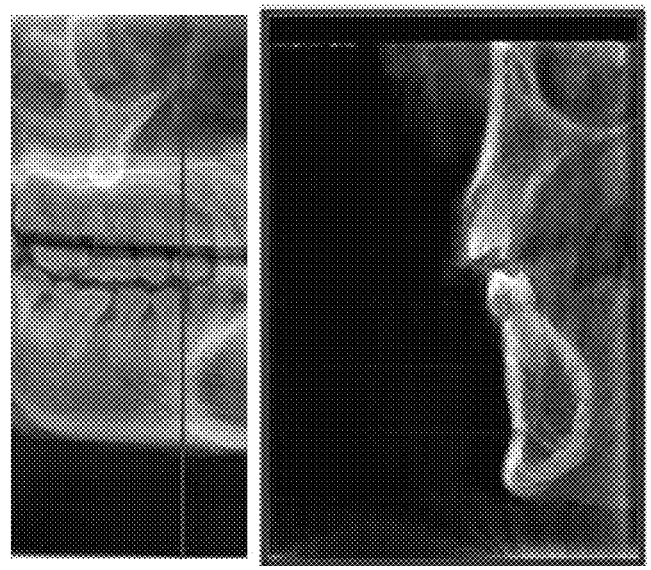
FIG. 14 illustrates an exemplary sectional image being acquired by an X-ray device according to an exemplary embodiment of the present invention.

In other words, when the examinee bites on the bite piece 122 while the aligning bite 100 is installed as shown in FIG. 8, projection data of the anterior teeth area $I_1$ may be acquired as shown in (a) of FIG. 13, and, when the examinee bites on the bite piece 122 while the aligning bite 100 is installed as shown in FIG. 9, projection data of the left molar area $I_2$ may be acquired as shown in (b) of FIG. 13, and, accordingly, a sectional image that is perpendicular to the dental arch may be acquired. FIG. 14 illustrates an example showing a sectional image being acquired by using the aligning bite and the X-ray device and, most particularly, the panoramic imaging device having the same according to the present invention.

As described above, the aligning bite of an X-ray device and the X-ray device having the same have the following advantages. According to the present invention, due to the joint structure of the aligning bite, since an area of interest requiring image information may be accurately aligned to an imaging focus area, accurate image information respective to the area of interest may be acquired, the operating range of the X-ray generator and the detector may be reduced and their driving mechanism may be simplified, and, furthermore, since the aligning direction of the subject is varied, and since there is no limitation in the available imaging range, the range of the area of interest that can be processed with imaging may be largely extended.

According to the present invention, since the height or thickness of the alveolar bone can be displayed after acquiring a sectional image of the area of interest, e.g., the anterior teeth area or the molar area, by using the panoramic imaging device, the cost of the X-ray device may be reduced, and the conventional panoramic imaging device may be directly used without modification.

Preferred embodiments of the present invention have been provided above, and it will be apparent to those skilled in the art that various modifications and variations can be made in the present invention without departing from the spirit or scope of the inventions.

Accordingly, the above-described embodiments of the present invention shall be understood only as exemplary embodiments that do not limit the scope of the present invention. Thus, it is intended that the present invention covers the modifications and variations of this invention provided they come within the scope of the appended claims and their equivalents.

What is claimed is:

1. As an aligning bite of an X-ray device for aligning a subject to an X-ray imaging point, the aligning bite of an X-ray device comprising:
    a support unit being rotatably connected to a bite stand supporting the aligning bite; and
    a bite unit being rotatably connected to the support unit, wherein the support unit comprises a link frame supporting the bite unit by connecting the bite unit to the bite stand, a first joint rotatably connecting one side of the link frame to the bite stand, a second joint rotatably connecting the bite unit to another side of the link frame, and a third joint being provided between the first joint and the second joint so as to allow the link frame to be folded.

2. The aligning bite of claim 1, wherein the link frame comprises:
    a first link member being connected to the bite stand by the first joint; and
    a second link member being connected to the first link member by the third joint.

3. The aligning bite of claim 2, wherein the second link member is connected to the bite unit by the second joint.

4. The aligning bite of claim 1, wherein the bite unit comprises:
    a bite support stand being rotatably connected to the link frame by the second joint; and
    a bite piece being mounted to the bite support stand so as to be bitten between upper teeth and lower teeth of an examinee (or subject of examination).

5. The aligning bite of claim 4, wherein the bite piece has an arched shape respective to a dental arch form.

6. The aligning bite of claim 4, wherein the bite piece is mounted to the bite support stand so as to allow a height of the bite piece to be adjusted.

7. The aligning bite of claim 5, wherein the bite support stand comprises a first bite mounting part and a second bite mounting part each supporting the bite piece at different heights.

8. The aligning bite of claim 4, wherein a plurality of pass-through holes is formed on the bite piece.

9. The aligning bite of claim 1, wherein a fastening holder is equipped to the support unit so as to simultaneously lock the first joint, the second joint, and the third joint.

10. The aligning bite of claim 9, wherein the fastening holder maintains a position of the aligning bite by simultaneously locking movements of the link frame and the bite unit.

11. An X-ray device, comprising:
an aligning bite of the X-ray device aligning a subject to an X-ray imaging point;
an X-ray generator emitting X-ray beams toward the subject; and
a detector moving while being in a state of facing into the X-ray generator, and
wherein the aligning bite comprises:
a support unit being rotatably connected to a bite stand supporting the aligning bite; and
a bite unit being rotatably connected to the support unit,
wherein the support unit comprises a link frame supporting the bite unit by connecting the bite unit to the bite stand, a first joint rotatably connecting one side of the link frame to the bite stand, a second joint rotatably connecting the bite unit to another side of the link frame, and a third joint being provided between the first joint and the second joint so as to allow the link frame to be folded.

12. The aligning bite of claim 2, wherein the bite unit comprises:
a bite support stand being rotatably connected to the link frame by the second joint; and
a bite piece being mounted to the bite support stand so as to be bitten between upper teeth and lower teeth of an examinee (or subject of examination).

13. The aligning bite of claim 3, wherein the bite unit comprises:
a bite support stand being rotatably connected to the link frame by the second joint; and
a bite piece being mounted to the bite support stand so as to be bitten between upper teeth and lower teeth of an examinee (or subject of examination).

* * * * *